US00PP10221P

United States Patent [19]

Sjulin et al.

[11] Patent Number: Plant 10,221

[45] Date of Patent: Feb. 3, 1998

[54] STRAWBERRY PLANT NAMED 'CORONADO'

[75] Inventors: Thomas M. Sjulin, Aromas; Amado Q. Amorao, Camarillo, both of Calif.

[73] Assignee: Driscoll Strawberry Associates, Inc., Watsonville, Calif.

[21] Appl. No.: 638,062

[22] Filed: Apr. 25, 1996

[51] Int. Cl.[6] ..... A01H 5/00

[52] U.S. Cl. ..... Plt./49

[58] Field of Search ..... Plt./48, 49

[56] References Cited

U.S. PATENT DOCUMENTS

P.P. 9,130 5/1995 Sjulin et al. ..... Plt./48

OTHER PUBLICATIONS

UPOVROM, Disk 96/03, Printout of Results 1 page.

*Primary Examiner*—Howard J. Locker
*Assistant Examiner*—Kent L. Bell
*Attorney, Agent, or Firm*—Pennie & Edmonds LLP

[57] ABSTRACT

This invention relates to a new and distinct variety of strawberry plant named 'Coronado', botanically identified as *Fragaria×ananassa*. The closest known variety is 'Balboa'. The new variety is partially everbearing. The new variety is distinguished from 'Balboa' by its globose plant habit, medium plant density, flat to cupped terminal leaflet profile, outwardly pointed petiole hairs, the inflorescence is held level to above the leaves, and the calyx is larger than the corolla. The harvest yield before April 1 of 'Coronado' is about 4.4 times greater than for 'Balboa' for the same period. The main crop of 'Coronado' is approximately one week before that of 'Balboa'. The PGI isozyme banding pattern for 'Coronado' is A2, while that for 'Balboa' is A1. The LAP banding pattern for both 'Coronado' and 'Balboa' is B3. The PGM banding pattern for 'Coronado' is C4, while that for 'Balboa' is C2. The reaction to disease is similar between 'Coronado' and 'Balboa', but 'Coronado' is moderately susceptible to Botrytis fruit rot, whereas 'Balboa' is susceptible.

3 Drawing Sheets

BACKGROUND OF THE INVENTION

The new variety of strawberry was discovered as a seedling in a controlled breeding plot in a cultivated area on the Rosemond Ranch in Oxnard, Ventura County, Calif., USA, in May, 1991. The seedling of the new variety was grown and asexually propagated by stolons in McArthur, Calif. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Coronado'. Among the characteristics which distinguish the new variety from other varieties of which we are aware are a combination of traits which include growth habit, leaf color, position of inflorescence relative to foliage, insertion of achenes, firmness of fruit flesh, evenness of color of fruit flesh, fruit texture and fruit acidity.

COMPARISON TO CLOSEST VARIETY

The variety which we believe to be closest to 'Coronado' from those known to us is 'Balboa' (U.S. Plant Pat. No. 9,130). There are several characteristics of the new variety that are different from, or not possessed by 'Balboa'. For example, the plant habit of 'Coronado' is globose, while 'Balboa' is flat. The plant density of 'Coronado' is medium while that of 'Balboa' is dense. Terminal leaflet profile of 'Coronado' is flat to cupped, while that of 'Balboa' is revolute. The petiole hairs of 'Coronado' point outward, while those of 'Balboa' point upward. The inflorescence of 'Coronado' is held level to above the leaves while the inflorescence of 'Balboa' is held below to level with the leaves. In 'Coronado', the calyx is larger than the corolla, while in 'Balboa' the calyx and corolla are approximately the same size.

In terms of harvest season, the yield before April 1 of 'Coronado' is about 4.4 times greater than for 'Balboa' for the same period. Furthermore, the main crop of 'Coronado' is approximately one week before that of 'Balboa'.

Regarding isozyme analysis, the PGI banding pattern for 'Coronado' is A2, while that for 'Balboa' is A1. The LAP banding pattern for both 'Coronado' and 'Balboa' is B3. The PGM banding pattern for 'Coronado' is C4, while that for 'Balboa' is C2. See J. Amer. Soc. Hort. Sci. 106: 684 (1981). The reaction to disease is similar between 'Coronado' and 'Balboa', but 'Coronado' is moderately susceptible to Botrytis fruit rot, whereas 'Balboa' is susceptible.

BRIEF DESCRIPTION OF THE ILLUSTRATIONS

The accompanying photographs show typical specimens of the new variety, including fruit, foliage and flower, in color as nearly true as it is reasonably possible to make in color illustrations of these characters.

DESCRIPTION OF THE NEW VARIETY

Figure 1:
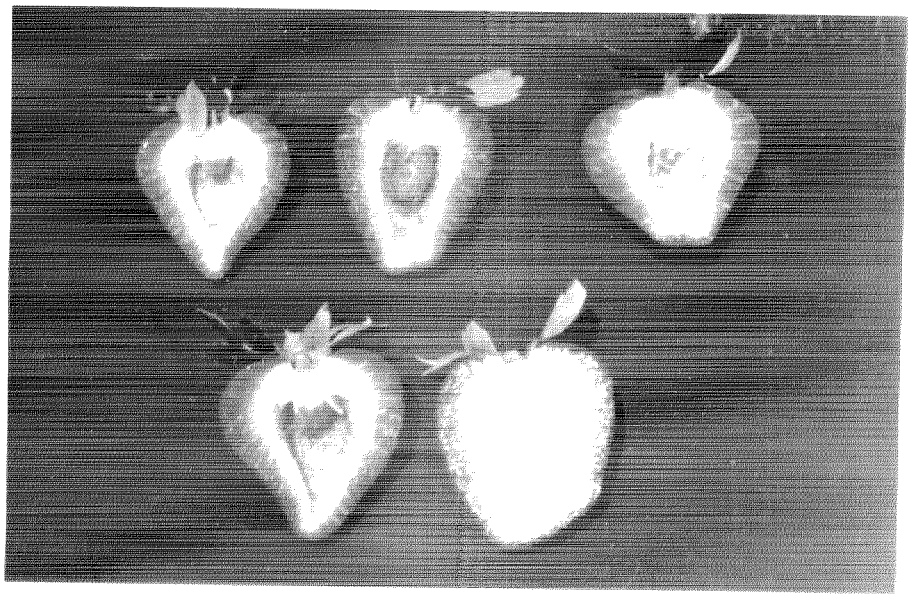
FIG. 1 shows typical fruit in longitudinal sections, illustrating the typical flesh and flesh coloration, conspicuous core and heart shape of the new variety.
Figure 2:
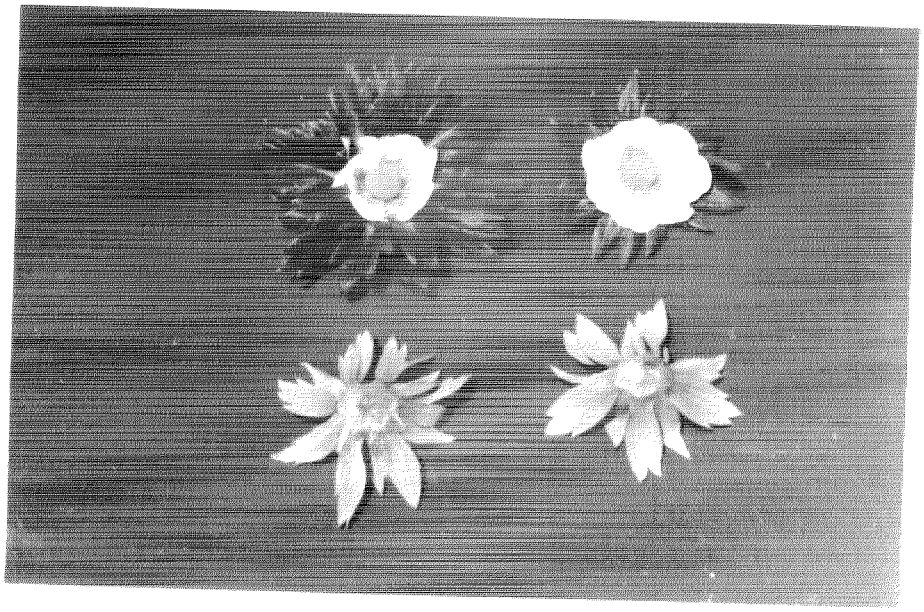
FIG. 2 shows the flower and reproductive organs of the new variety, as well as the size and position of the petals and sepals and the underside of the calyx.
Figure 3:
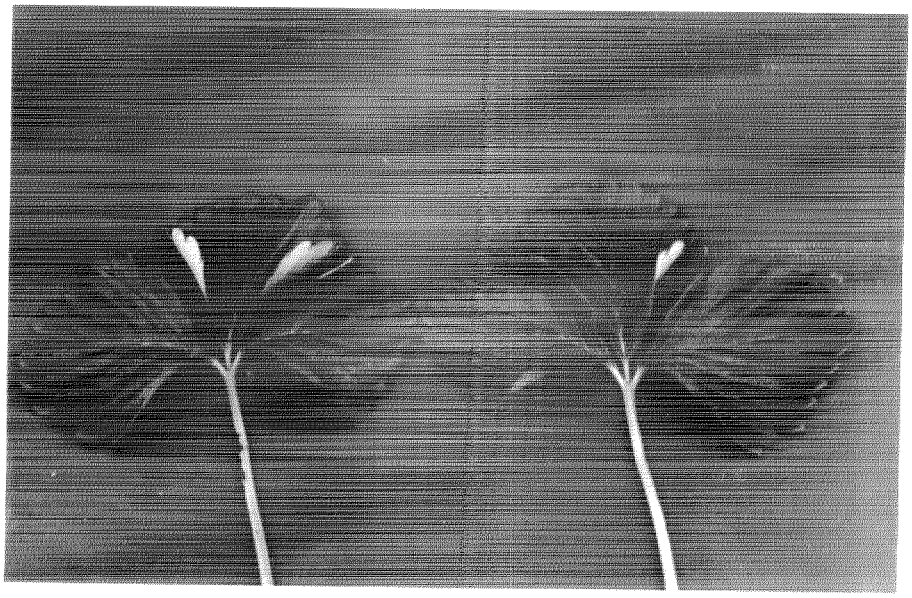
FIG. 3 shows the upper surface of two typical folioles of the new variety.

The following detailed description of the new variety is based upon observations taken of plants and fruit grown in experimental test plots in Ventura County, Calif., U.S.A. in 1995. The strawberry varieties 'Coronado' and 'Balboa' were evaluated in a side-by-side comparison under similar conditions in a forcing system. In 1995, 'Coronado' was first harvested the week of February 18. The last harvest occurred the week of June 10. These harvest dates are for the Donlon Ranch in Oxnard, Ventura County, Calif. This description is in accordance with UPOV terminology, and the color terminology herein is in accordance with the Munsell Notation. Color designations, color descriptions, and other phenotypical descriptions may deviate from the stated values and descriptions depending upon variation in environmental, seasonal, climatic and cultural conditions.

Propagation

The new variety is principally propagated by way of stolons. Although propagation by stolons is presently preferred, other known methods of propagating strawberry plants may be employed. It has been determined that the plants root well after transplanting.

Characteristics of the New Variety

The following information is provided to describe the new variety.

Plant:

*Habit.*—Globose.

*Density.*—Medium.

*Vigor.*—Medium.

Foliage:

*Leaf.*—Color — Upperside — light to medium green, 7.4 GY 2.3/4.0. Profile (angle of leaf where attached to petiole) — slightly concave. Blistering — medium to strong. Number of leaflets — more than three (on up to 5 out of 10 leaves).

*Terminal leaflet.*—Profile — flat to cupped. Length to width ratio — from as long as broad to longer than broad. Shape of base — obtuse. Shape of teeth — rounded.

*Petiole.*—Pubescence — medium. Pose of hairs — outward.

*Stolons.*—Number — medium to many. Anthocyanin coloration — weak to medium. Thickness — medium. Pubescence — sparse to medium.

*Inflorescence.*—Level with to above foliage.

Flower:

*Petal color.*—White; White is not referenced on the "Munsel Color Cascade".

*Size.*—Medium. 'Coronado' has an average flower diameter of 28.8 mm, with a range from 20 to 37 mm.

*Diameter of calyx relative to corolla.*—Larger.

*Diameter of inner calyx relative to outer (on secondary flowers).*—Smaller.

*Spacing of petals (on secondary flowers with 5 or 6 petals).*—Touching to overlapping.

*Petal length to width ratio (on secondary flowers).*—As long as broad.

*Fruiting truss.*—Attitude at first picking — semi-erect to prostrate. Length — long.

Fruit — (secondary fruit on one year old plants): Strawberry plants possess a branching inflorescence, or peduncle, having a primary (first) flower which is the largest and secondary flowers which are on the lateral branches. "Secondary fruit" are those that develop from secondary flowers which develop from lateral buds on the peduncle. One year old plants are those which are in their first year in the fruiting field.

*Ratio of length to maximum width.*—Longer than broad.

*Size.*—Large.

*Predominant shape.*—Conical to wedged.

*Difference in shapes between primary and secondary fruits.*—Moderate.

*Band without achenes.*—Absent or very narrow.

*Unevenness of surface.*—Weak to medium.

*Skin color.*—Red to dark red, 7.9R 2.9/9.5.

*Evenness of color.*—Even.

*Glossiness.*—Medium.

*Insertion of achenes.*—Below surface.

*Insertion of calyx.*—Level to set above fruit.

*Pose of the calyx segments.*—Reflexed.

*Size of calyx in relation to fruit diameter.*—Larger.

*Adherence of calyx.*—Weak to medium.

*Firmness of flesh (when fully ripe).*—Medium.

*Color of flesh.*—Light red and white — 8.4R 2.9/9.4.

*Evenness of color of flesh.*—Uneven.

*Sweetness.*—Medium.

*Texture when tasted.*—Medium.

*Acidity.*—Medium.

Time of flowering (50% of plants at first flower): Very early to early.

Harvest maturity (50% of plants with ripe fruit): Very early to early.

Type of bearing: Partially everbearing. Partially everbearing varieties will continue to re-flower and fruit under cool conditions, such as those that occur in Coastal California. These varieties stop flowering under warm conditions.

Disease Resistance and Susceptibility

The 'Coronado' variety is susceptible to *Xanthamonas fragariae*, Verticillium wilt, and the anthracnose disease caused by *Collectotrichum acutatum*. 'Coronado' is moderately resistant to powdery mildew and aphid-borne virus diseases.

The 'Coronado' strawberry fruit is moderately susceptible to decay by *Botrytis cinerea* and Rhizopus spp.

The 'Coronado' plant is susceptible to injury by the two-spotted spider mite (*Tetranychus urticae*), cyclamen mite (*Phytonemus pallidus*), and lygus bug (*Lygus hesperus*).

What is claimed is:

1. A new and distinct variety of strawberry plant, substantially as shown and described.

* * * * *